US008945037B2

(12) United States Patent
Hasegawa et al.

(10) Patent No.: US 8,945,037 B2
(45) Date of Patent: Feb. 3, 2015

(54) BLOOD PURIFICATION APPARATUS

(71) Applicant: Nikkiso Company Limited, Tokyo (JP)

(72) Inventors: Shinya Hasegawa, Makinohara (JP); Masahiro Toyoda, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 13/625,315

(22) Filed: Sep. 24, 2012

(65) Prior Publication Data

US 2013/0023812 A1 Jan. 24, 2013

Related U.S. Application Data

(63) Continuation of application No. PCT/JP2011/057161, filed on Mar. 24, 2011.

(30) Foreign Application Priority Data

Mar. 25, 2010 (JP) ................................. 2010-070148

(51) Int. Cl.
*A61M 1/34* (2006.01)
*A61M 1/16* (2006.01)
(Continued)

(52) U.S. Cl.
CPC .............. *A61M 1/342* (2013.01); *A61M 1/3434* (2014.02); *A61M 1/3612* (2014.02); *A61M 2230/207* (2013.01); *A61M 1/3455* (2013.01);
(Continued)

(58) Field of Classification Search
CPC ..... A61M 1/16; A61M 1/342; A61M 1/3441; A61M 1/3455; A61M 1/3462; A61M 2001/3431; A61M 2001/3434; A61M 2001/361; A61M 2001/3612; A61M 2001/3609; A61M 2001/3658; A61M 2001/1613; A61M 2001/1601; A61M 2001/1615; A61M 2001/3465; A61M 2230/207; A61M 1/3663; A61M 2205/3327; A61M 2205/3351; Y10S 210/929; B01D 61/14; B01D 61/145; B01D 61/18; B01D 61/20; B01D 61/22; B01D 61/24; B01D 61/28; B01D 61/30; B01D 61/32
USPC ............. 604/4.01, 5.01, 5.04, 6.01, 6.09, 6.1, 604/6.11; 422/44
See application file for complete search history.

(56) References Cited

U.S. PATENT DOCUMENTS 5,366,630 A * 11/1994 Chevallet ...................... 210/645
5,698,090 A * 12/1997 Bene et al. ...................... 210/85
(Continued)

FOREIGN PATENT DOCUMENTS

DE     42 40 681     6/1994
JP     08-191889     7/1996
(Continued)

*Primary Examiner* — Adam Marcetich
(74) *Attorney, Agent, or Firm* — Harness, Dickey & Pierce, P.L.C.

(57) ABSTRACT

A blood purification apparatus has a dialyzer (1), an arterial blood circuit (2) with a blood pump 4, a venous blood circuit 3, a dialysate introduction line L1, a dialysate discharge line L2, a substitution line L3, and a substitution pump 9 that supplies the dialysate flowing in the substitution line L3 to the arterial blood circuit 2. A control device (11) estimates or measures the concentration of blood in a dilution channel section A. The control device (11) controls the volume of dialysate supplied by the substitution pump 9 on the basis of the estimated or measured blood concentration.

7 Claims, 4 Drawing Sheets

(51) Int. Cl.
  *A61M 1/14* (2006.01)
  *A61M 1/36* (2006.01)

(52) U.S. Cl.
  CPC ......... *A61M1/3609* (2014.02); *A61M 1/3441* (2013.01); *A61M 1/1613* (2014.02); *A61M 1/1601* (2014.02); *A61M 2205/3351* (2013.01); *A61M 1/16* (2013.01); *A61M 1/3462* (2013.01); *A61M 2205/3327* (2013.01); *A61M 1/3431* (2014.02); *A61M 1/3465* (2014.02); *A61M 1/361* (2014.02)
  USPC ....... 604/6.09; 604/4.01; 604/5.01; 604/5.04; 604/6.01; 604/6.11; 422/44

(56) References Cited

U.S. PATENT DOCUMENTS

| | | | |
|---|---|---|---|
| 5,725,775 A * | 3/1998 | Bene et al. | 210/646 |
| 6,406,631 B1 * | 6/2002 | Collins et al. | 210/646 |
| 2002/0023880 A1 * | 2/2002 | Pedrini et al. | 210/646 |
| 2002/0104800 A1 * | 8/2002 | Collins et al. | 210/646 |
| 2004/0068219 A1 * | 4/2004 | Summerton et al. | 604/5.01 |
| 2004/0129616 A1 | 7/2004 | Mori et al. | |
| 2004/0168988 A1 * | 9/2004 | Ikeda | 210/744 |
| 2005/0065459 A1 * | 3/2005 | Zhang et al. | 604/4.01 |
| 2005/0095171 A1 * | 5/2005 | Fressinet et al. | 422/44 |
| 2005/0133449 A1 * | 6/2005 | Sternby | 210/645 |
| 2005/0251086 A1 * | 11/2005 | Sternby | 604/4.01 |
| 2006/0009727 A1 | 1/2006 | O'Mahony et al. | |
| 2007/0108128 A1 * | 5/2007 | Kopperschmidt et al. | 210/646 |
| 2007/0161941 A1 * | 7/2007 | Ash et al. | 604/6.09 |
| 2008/0015486 A1 * | 1/2008 | Zhang et al. | 604/4.01 |
| 2008/0015487 A1 | 1/2008 | Szamosfalvi et al. | |
| 2008/0149563 A1 | 6/2008 | Ash | |
| 2008/0215247 A1 * | 9/2008 | Tonelli et al. | 702/19 |
| 2008/0275377 A1 * | 11/2008 | Paolini et al. | 604/6.11 |
| 2009/0054822 A1 * | 2/2009 | Murakami et al. | 604/6.1 |
| 2010/0114002 A1 | 5/2010 | O'Mahony et al. | |
| 2010/0137777 A1 * | 6/2010 | Kopperschmidt | 604/5.04 |
| 2010/0168640 A1 * | 7/2010 | Kopperschmidt et al. | 604/6.09 |
| 2010/0264086 A1 | 10/2010 | Noack et al. | |
| 2010/0276367 A1 | 11/2010 | Zhang | |
| 2010/0280430 A1 * | 11/2010 | Caleffi et al. | 604/5.01 |
| 2011/0098625 A1 * | 4/2011 | Masala et al. | 604/6.09 |

FOREIGN PATENT DOCUMENTS

| | | |
|---|---|---|
| JP | 11-276575 | 10/1999 |
| JP | 2001-112863 | 4/2001 |
| JP | 2002-503115 | 1/2002 |
| JP | 2002-165877 | 6/2002 |
| JP | 2004-174235 | 6/2004 |
| JP | 2004-313522 | 11/2004 |
| JP | 2009-527343 | 7/2009 |
| WO | WO96/25214 | 8/1996 |
| WO | WO2009/056325 | 5/2009 |
| WO | WO2009/087092 | 7/2009 |

* cited by examiner

BLOOD PURIFICATION APPARATUS

CROSS-REFERENCE TO RELATED APPLICATIONS

This application is a continuation of International Application No. PCT/JP2011/057161, filed Mar. 24, 2011, which claims priority to Japanese Application No. 2010-070148, filed Mar. 25, 2010. The disclosures of the above applications are incorporating herein by reference.

FIELD

The present disclosure relates to a blood purification apparatus that performs blood purification treatments using a blood purifier connected to a blood circuit.

BACKGROUND

Recently, in dialysis apparatus used as a blood purification apparatus, a technique has been suggested that performs priming, reinfusion, and substitution (emergency substitution) using a dialysate to be supplied to a dialyzer during dialysis treatment (particularly, an on-line HDF or an on-line HF). For example, Japanese Laid-open Patent Application No. 2004-313522 discloses a dialysis apparatus that includes a substitution line that has one end connected to a collection port formed in a predetermined part of a dialysate introduction line. The other end is connected to a blood circuit (arterial blood circuit or venous blood circuit). A substitution pump is disposed in the substitution line. In order to perform the priming, the reinfusion or the substitution (the emergency substitution) using the dialysis apparatus, the dialysate in a dialysate introduction line is supplied to the blood circuit (the arterial blood circuit or the venous blood circuit) by driving the substitution pump.

However, in a blood purifier (hereinafter, called an on-line HDF) that is applied to the blood dialysis filtration (HDF) and uses the dialysate as the substitution, there is a need to perform the substitution (including a pre-substitution performing substitution by the arterial blood circuit, and a post-substitution performing substitution by the venous blood circuit) of the dialysate to the patient's blood by ultrafiltration corresponding to a filtration treatment as the HDF treatment. As an apparatus applied to the on-line HDF, as disclosed in Japanese Laid-open Patent Application No. 2001-112863, a dialysis apparatus has been suggested that has a dialyzer, a blood circuit constituted by an arterial blood circuit and a venous blood circuit with a blood pump. A dialysate introduction line introduces the dialysate into the dialyzer. A dialysate discharging line discharges the dialysate from the dialyzer. A substitution line (a pre-substitution line or a post-substitution line) supplies the dialysate of the dialysate introduction line to the blood circuit to perform the substitution without going through the dialyzer.

In the dialysis apparatus that has the pre-substitution line, which is able to perform the pre-substitution, and since the patient's blood circulating extracorporeally is subjected to the substitution before reaching the dialyzer, in the dialyzer, the blood diluted by the substitution is filtrated. Thus, in general, the dialysis apparatus performing the pre-substitution can drive the substitution pump more rapidly than devices that perform post-substitution. Thus, it can sufficiently perform the dilution using the substitution.

However, in the blood purification apparatus performing the pre-substitution of the related art described above, problems exist. Just after the blood purification is started, or just after the driving is started after stopping the substitution pump once, the dialysate, as the substitution, is not supplied to a channel (hereinafter, such a part is called a "dilution channel section") in the arterial blood circuit. Thus, sufficient dialysate is not supplied, the dilution is insufficient, and the blood, with high concentration, flows between a connection part to the substitution line in the arterial blood circuit and the dialyzer.

Meanwhile, a predetermined amount of dialysate, as the substitution, is supplied to the arterial blood circuit from the dialysate introduction line. A flow rate of the dialysate introduced into the dialyzer is reduced by the flow rate supplied as the substitution that the dialysate discharged from the dialyzer. Thus, even if there is no driving of the ultrafiltration pump or the like, filtration is performed using the dialyzer. As a result, there has been a concern that the blood with insufficient dilution may be further filtrated. Thus, there is a problem that the blood circulating extracorporeally is excessively concentrated. Furthermore, as described above, the fluid purification apparatus performing the pre-substitution is configured so as to drive the substitution pump faster than a case of performing the post-substitution. Thus, there is a disadvantage that the excessive concentration is easily generated.

SUMMARY

The present disclosure has been made under such circumstances. It is an object to provide a blood purification apparatus that is able to prevent excessive concentration of the blood circulating extracorporeally when performing the post-substitution.

According to the disclosure, a blood purification apparatus is provided that includes a blood purifier that includes a blood purification membrane and performs blood purification in the blood purification membrane. An arterial blood circuit has a proximal end connected to the blood purifier. A blood pump is disposed in the arterial blood circuit. A venous blood circuit has a proximal end connected to the blood purifier. A dialysate introduction line introduces a dialysate into the blood purifier. A dialysate discharge line discharges the dialysate from the blood purifier. A substitution line has an end connected to a substitution source and the other end connected to the arterial blood circuit. A substitution supplying device supplies the substitution flowing in the substitution line to the arterial blood circuit. The apparatus further includes a control device capable of assuming or measuring a blood concentration of a dilution channel section formed by a channel from a connection part with the substitution line in the arterial blood circuit to the blood purifier. The controller is capable of controlling the flow rate of the substitution supplied by the substitution supplying device based on the assumed or measured blood concentration.

The apparatus further includes a calculation device that calculate a time when blood diluted by the supplying of the substitution to the dilution channel section reaches the blood purifier and assumes the blood concentration in the dilution channel section. The control device is capable of controlling the flow rate of the substitution supplied by the substitution supplying device depending on the blood concentration determined by the calculation device.

The calculation device calculates a change in concentration of the blood by an operation formula that uses at least one of the flow rate of the blood circulating extracorporeally by the driving of the blood pump, capacity of the dilution channel section, an ultrafiltration flow rate that is an ultrafiltration rate from the blood, an allowance value that can be filtered by the blood purifier, and an objective supply flow rate of the substitution using the substitution supplying device as a parameter.

The apparatus further includes a measurement device to measure the blood concentration in the dilution channel section. The control device is able to control the flow rate of the substitution supplied by the substitution supplying device depending on the blood concentration measured by the measurement device.

The measurement device includes a blood densitometer of a sensor. The blood densitometer is capable of measuring the blood concentration in the dilution channel section. The sensor measures the parameter change according to the change of the blood concentration.

The control device is capable of increasing, stepwise, and controlling the flow rate of the substitution supplied by the substitution supplying device.

Alternatively, the control device is capable of continuously increasing and controlling the flow rate of the substitution supplied by the substitution supplying device.

According to the disclosure, it is possible to determine or measure the blood concentration of the dilution channel section. Thus, it is possible to control the flow rate of the substitution supplied by the substitution supplying device based on the assumed or measured blood concentration. Thus, it is possible to prevent the excessive concentration of the blood circulating extracorporeally when performing the post-substitution.

The control device is able to increase, stepwise, and control the flow rate of the substitution supplied by the substitution supplying device. Thus, it is possible to more simply and easily perform the control of the flow rate of the substitution based on the blood concentration of the dilution channel section.

The control device is able to continuously increase and control the flow rate of the substitution supplied by the substitution supplying device. Thus, it is possible to more smoothly and accurately perform the control of the flow rate of the substitution based on the change of the blood concentration of the dilution channel section.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Hereinafter, an embodiment of the present disclosure will be specifically described with reference to the drawings.

Figure 1:
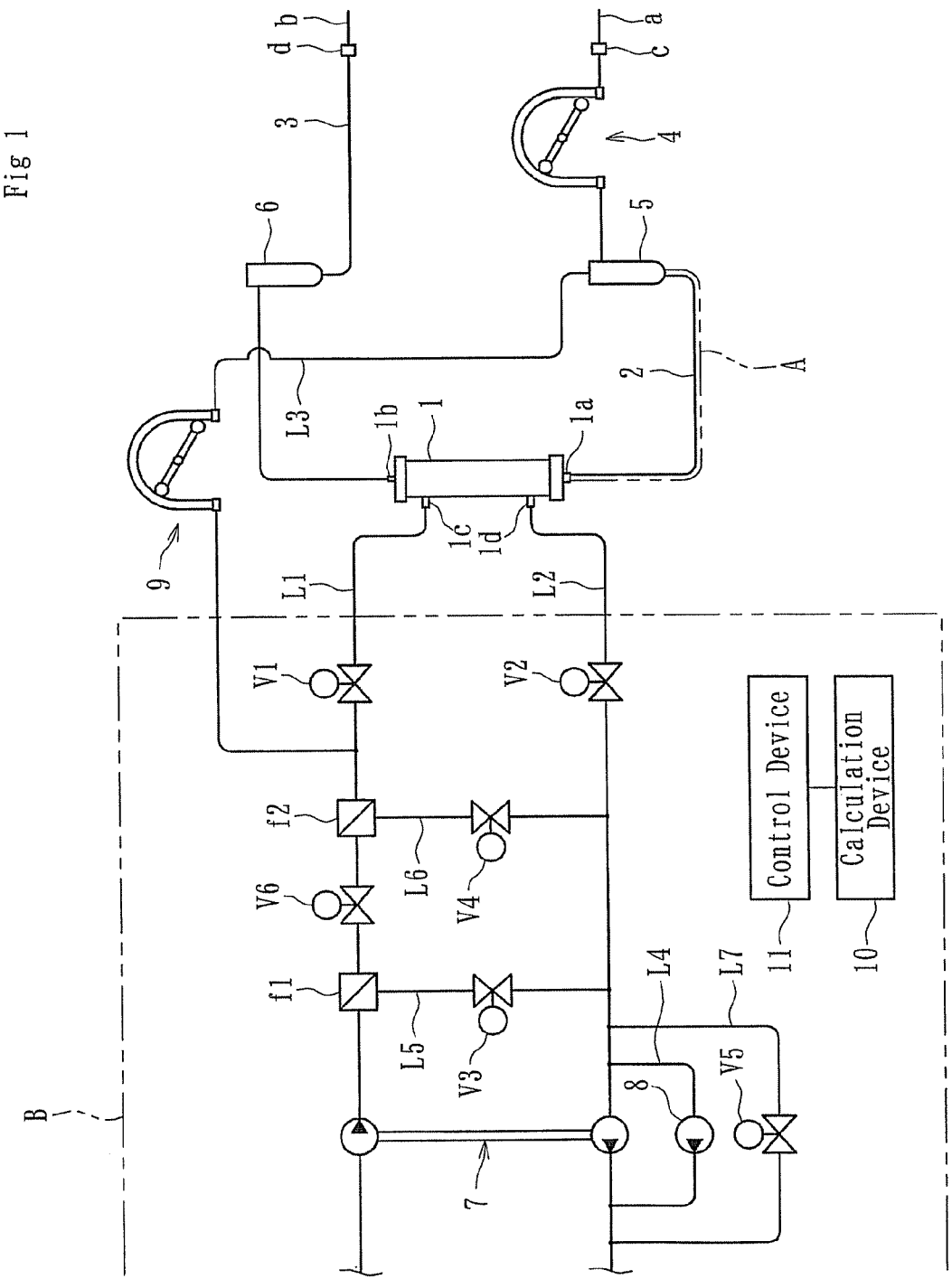
FIG. 1 is a schematic diagram of a dialysis apparatus according to a first embodiment.

A blood purification apparatus according to the present embodiment is applied to a blood dialysis apparatus (on-line HDF) that performs a pre-substitution that supplies a dialysate as a substitution (substitution fluid) to an arterial blood circuit 2 in the blood purification treatment process. As shown in FIG. 1, the blood purification apparatus includes a blood circuit where the arterial blood circuit 2 and a venous blood circuit 3 are connected to a dialyzer 1 as a blood purifier. The blood purification, apparatus also includes a dialysis apparatus main body B having a dialysate introduction line L1 and a dialysate discharging line L2, a substitution line L3, a substitution pump 9 as a substitution supplying device, a calculation device 10, and a control device 11.

The dialyzer 1 includes a blood purification membrane (not shown). Although the membrane is a hollow fiber type blood dialysis filtration membrane in the present embodiment, the membrane may include a flat membrane type, a blood dialysis membrane and a blood filtration membrane. The dialyzer 1 is formed with a blood introduction port 1a to introduce the blood. A blood discharge port 1b delivers the introduced blood. A dialysate introduction port 1c introduces the dialysate. A dialysate discharge port 1d discharges the introduced dialysate. The dialyzer 1 purifies the blood by bringing the dialysate into contact with the blood introduced from the blood introduction portion 1a, via the hollow fiber.

The arterial blood circuit 2 includes a flexible tube. One end of the tube is connected to the blood introduction portion 1a of the dialyzer 1 to guide the blood collected from a patient's blood vessel into the hollow fiber of the dialyzer 1. The other end of the arterial blood circuit 2 includes a connector (c) capable of attaching an arterial puncture needle (a). An arterial air trap chamber 5 is connected to the middle of the tube. A blood pump 4 is disposed along the tube. Furthermore, the blood pump 4 is a peristaltic pump with a configuration that squeezes the flexible tube during normal rotation to cause the blood from the arterial puncture needle (a) to flow in a direction of the blood introduction port 1a of the dialyzer 1.

The venous blood circuit 3 includes the flexible tube as in the arterial blood circuit 2. One end is connected to the blood introduction port 1b of the dialyzer 1 to deliver the blood passing through the hollow fiber. The other end of the venous blood circuit 3 includes a connector (d) capable of attaching a venous puncture needle (b). A venous air trap chamber 6 is connected to the middle of the tube. Furthermore, the patient's blood collected by the arterial puncture needle (a) reaches the dialyzer 1, via the arterial blood circuit 2, flows through the venous blood circuit 3, after the blood purification is performed, and returns to the body of the patient, via the venous puncture needle (b). Thus, the extracorporeal circulation is performed.

The dialysate introduction line L1 and the dialysate discharge line L2 are connected to the dialysate introduction port 1c and the dialysate discharge port 1d of the dialyzer 1, respectively. The dialysate introduced to the dialyzer 1 via the dialysate introduction line L1 can be discharged from the dialysate discharge line L2 through the outside of the hollow fiber membrane. Electromagnetic valves V1 and V2 are connected to the middle of the dialysate introduction line L1 and the dialysate discharge line L2, respectively.

Furthermore, a duplex pump 7 is connected to the dialysate introduction line L1 and the dialysate discharge line L2. The duplex pump 7 supplies the dialyzer 1 with the dialysate prepared to a predetermined concentration and discharges the dialysate from the dialyzer 1. Furthermore, bypass lines L5 and L6 are disposed in the dialysis apparatus main body B. The bypass lines L5, L6 enable the dialysate introduction line L1 and the dialysate discharge line L2 to communicate with each other. Electromagnetic valves V3 and V4 are disposed in the middle of the bypass lines L5 and L6, respectively. In the drawings, reference numerals f1 and f2 indicate filtration filters disposed in the dialysate introduction line L1. An electromagnetic valve V6 is disposed between the filtration filters f1 and f2.

The dialysate discharge line L2 is formed with bypass lines L4 and L7 that bypass the duplex pump 7. An ultrafiltration pump 8, to ultrafiltrate the patient's blood flowing in the dialyzer 1, is disposed in the bypass line L4. The electromagnetic valve V5, capable of opening or closing the channel, is disposed in the bypass line L7. During blood purification treatment, the dialysate can be supplied to the dialyzer 1 and the arterial air trap chamber 5. In this state, the electromagnetic valves V1, V2 and V6 are in the opened state and the electromagnetic valves V3 and V4 are in the closed state.

One end of the substitution line L3 is connected to a collection port (not shown) formed at a predetermined location (the substitution source) of the dialysate introduction line L1. Thus, the dialysate (substitution) can flow in from one end. The other end includes a channel (for example, a flexible tube or the like) connected to the top of the arterial air trap chamber 5. The collection portion includes a port formed in the dialysis apparatus main body B. The dialysate introduction line L1 and the arterial air trap chamber 5 are able to communicate with each other, by connecting one end of the substitution line L3 to the collection port.

Although the substitution line L3, according to the present embodiment, is connected to the arterial air trap chamber 5, the substitution line L3 may be connected to another part, for example, directly to the channel constituting the arterial blood circuit 2 via the connection member such as a T-shaped pipe, of the arterial blood circuit 2. In the present disclosure, a channel between the connection part (the arterial air trap chamber 5 in the present embodiment) to the substitution line L3 in the arterial blood circuit 2 and the dialyzer 1 (the blood purifier) is defined as a "dilution channel section A".

The substitution pump 9, forming the substitution supplying device, is disposed in the substitution line L3. The substitute pump 9 supplies the dialysate (substitution) flowing in the substitution line L3 to the arterial blood circuit 2, via the arterial air trap chamber 5. As a result, one end of the substitution line L3 is connected to the dialysate introduction line L1 and the other end is connected to the arterial air trap chamber 5, respectively. By driving, normal rotation, the substitution pump 9, it is possible to perform the pre-substitution in the blood purification treatment process. This includes supplying a substitution form that supplies the dialysate as the substitution to the arterial blood circuit 2. Furthermore, as in the blood pump 4, the substitution pump 9 is a peristaltic pump. The pump 9 has a configuration that can squeeze the tube constituting the substitution line L3 when being driven to enable the dialysate to flow.

However, the substitution line L3 is disposed with a clamp device (not shown) capable of opening and closing the channel. After the substitution line L3 is connected to the collection port by a worker, the clamp device is in the closed state until the dialysate is caused to circulate, and the channel is closed. Moreover, if necessary during priming, reinfusion, substitution or the like, the clamp device is in the open state by a worker, the dialysate introduction line L1 communicates with the blood circuit, the arterial blood circuit 2.

The calculation device 10 calculates time when the blood diluted by the supplying of the dialysate (the substitution) to the dilution channel section (A) reaches the dialyzer 1. The calculation device 10 determines the blood concentration of the dilution channel section (A) and performs the calculation as below. Thus, the calculation device 10 calculates the time when the blood diluted, by the supplying of the dialysate (the substitution) to the dilution channel section A, reaches the dialyzer 1. It is calculated by a predetermined calculation formula utilizing the following parameters: the blood flow rate (blood flow) circulating extracorporeally by the driving of the blood pump 4; the capacity of the dilution channel section A; the ultrafiltration flow rate that is the ultrafiltration rate from the blood; the allowance value (in the present embodiment, the allowed maximum value that is the ratio of the filtrate to the blood) that can be filtered by the dialyzer 1; and the object supply flow rate of the dialysate (the substitution) using the substitution pump 9 (the substitution supplying device). Thus, the blood concentration of the dilution channel section A is assumed.

Specifically describing using the specific numerical values is as follows: when the blood flow rate (the blood flow) is 200 (mL/min), the capacity of the dilution channel section A is 20 (mL), the ultrafiltration flow rate (the ultrafiltration rate) is 10 (mL/min), an allowance ratio (a ratio of the filtrate to the blood flow) capable of being filtered by the dialyzer 1 is 20(%), and the object substitution rate is 200 (mL/min), since the ratio of the filtrate to the blood is 20(%), the maximum filtrate (the limit of the filtrate) obtainable from the blood is 200 (mL/min)×0.2=40 (mL/min) under these conditions.

Thus, the result is calculated where the maximum value (the limit) of the substitution rate is 30 (mL/min) from the maximum filtrate (the limit of the filtrate) obtainable from the blood of 40 (mL/min) and the ultrafiltration rate of 10 (mL/min). Thus, as an initial step, the substitution pump 9 is driven at the flow rate of 30 (mL/min). At this time, the flow rate of the dilution channel section A is 200 (mL/min)+30 (mL/min)= 230 (mL/min) from "blood flow rate+the flow rate of the substitution". The time when the blood diluted by the dialysate reaches the dialyzer 1 is calculated as 20 (mL)÷230≅0.087 (min)≅5.2 (sec) from "the capacity of the dilution channel section A÷ flow rate of the dilution channel section A".

That is, since the diluted blood reaches the dialyzer 1 when the elapsed time is 5.2 seconds after the substitution is started at 30 (mL/min), the substitution rate (30 (mL/min)) of the diluted blood can be further added. In the present embodiment, the substitution rate can be increased up to 60 (mL/min). Thus, at the next stage, the substitution pump 9 is driven at the flow rate of 60 (mL/min). At this time, the flow rate of the dilution channel section A is 200 (mL/min)+60 (mL/min)=260 (mL/min) from "the blood flow rate+the flow rate of the substitution". The time when the blood diluted by the dialysate reaches the dialyzer 1 is calculated as 20 (mL)÷260≅0.077 (min)≅4.6 (sec) from "the capacity of the dilution channel section A÷ flow rate of the dilution channel section A".

Figure 2:
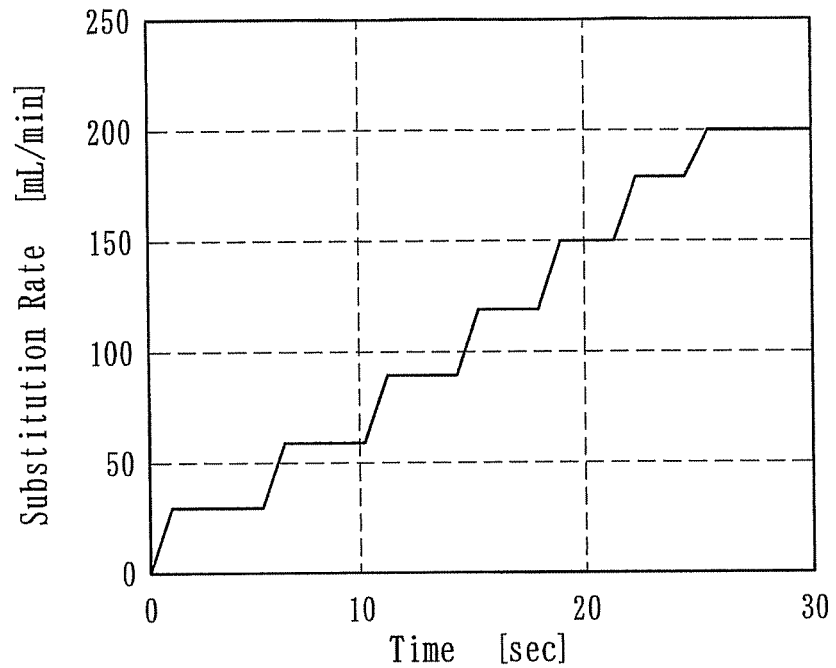
FIG. 2 is a graph that shows control contents (controls stepwise the flow rate of the dialysate (the substitution) supplied by the substitution supplying device) using the control device in the dialysis apparatus.

Hereinafter, by repeating the calculation described above, the substitution rate is increased until reaching the object substitution rate (200 (mL/min) in the present embodiment). In the present embodiment, although the substitution rate in increased by 30 (mL/min), since the flow rate in the dilution channel section A is also increased accordingly, the reaching time of the diluted blood is gradually shorted, and as shown in FIG. 2. The graph of the substitution rate to the time is changed in a soaring stair shape.

In this manner, if the calculation device 10 calculates the time when the blood diluted by the supplying of the dialysate (the substitution) to the dilution channel section (A) reaches the dialyzer 1, if the reaching time (5.2 (sec), 4.6 (sec), . . . in the calculation described above) elapses, the degree of the dilution (concentration) of the dilution channel section (A) can be determined. Thus, the blood concentration of the dilution channel section A can be assumed. In the present embodiment, it is assumed whether or not a suitable blood concentration is obtained from the degree of the dilution.

The control device 11 includes, for example, a microcomputer or the like capable of controlling the opening and the closing of various electromagnetic valves V1 to V6 disposed in the dialysis apparatus and an actuator of the blood pump 4, the substitution pump 9 or the like. Particularly, in the present embodiment, the control device 11 is electrically connected to the calculation device 10. The calculation device 11 is able to control the flow rate of the dialysate (the substitution) supplied by the substitution pump 9 (the substitution supplying device) based on the blood concentration assumed by the calculation device 10 or measured by the measurement device as in the second embodiment.

Specifically, the calculation device 10 sequentially calculates the time when the blood diluted by the supplying of the dialysate to the dilution channel section A reaches the dialyzer 1, as shown in FIG. 2. Thus, it is possible to control the flow rate of the dialysate (the substitution) supplied by the substitution pump 9 (the substitution supplying device) of each stage. In the present embodiment, as shown in FIG. 2, the control device 11 can increase, stepwise, and control the flow rate of the dialysate (the substitution) supplied by the substitution pump 9 (the substitution supplying device). Thus, it is possible to more simply and easily perform the control of the flow rate of the dialysate based on the blood concentration of the dilution channel section (A).

Figure 3:
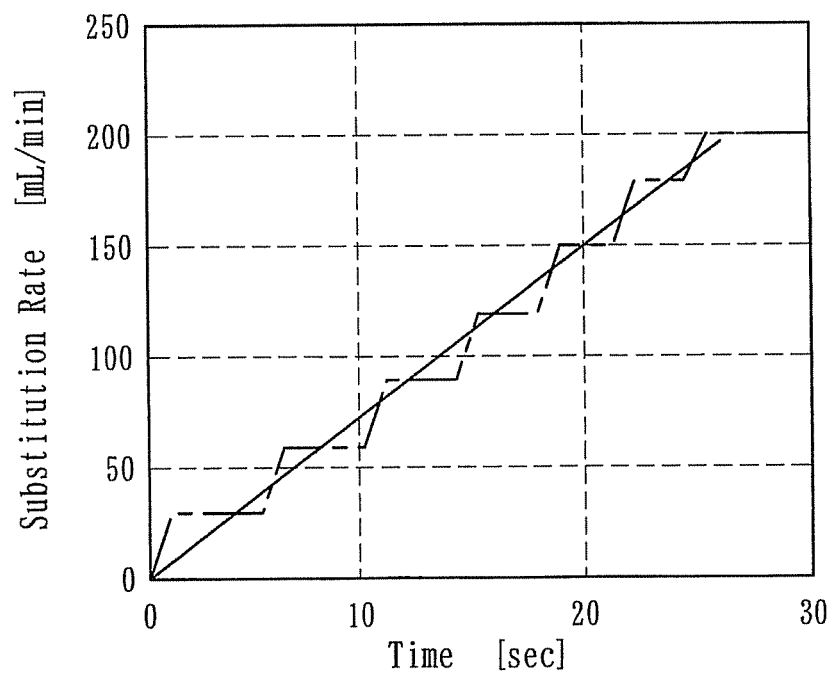
FIG. 3 is a graph that shows control contents (controls stepwise the flow rate of the dialysate (the substitution) supplied by the substitution supplying device) using the control device in the dialysis apparatus.

Furthermore, as shown in FIG. 3, the control device 11 may continuously increase the flow rate of the dialysate (the substitution) supplied by the substitution pump 9 (the substitution supplying device). Thus, it increases the flow rate along a straight line or a curve, as shown in FIG. 3, instead of increasing, stepwise, the flow rate of the dialysate (the substitution) as described above. In this case, it is possible to more smoothly and accurately perform the control of the flow rate of the dialysate (the substitution) based on a change in blood concentration of the dilution channel section (A). Furthermore, the straight line or the curve of FIG. 3 is approximated based on the stepwise graph of FIG. 2.

According to the described above embodiment, the blood concentration of the dilution channel section (A) can be assumed. The flow rate of the dialysate (the substitution) supplied by the substitution pump 9 (the substitution supplying device) based on the assumed blood concentration can be controlled by the control device 11. Thus, when performing the pre-substitution, the excessive concentration of the blood circulating extracorporeally can be prevented. In the present embodiment, the blood concentration of the dilution channel section A is assumed by calculating the time when the blood diluted by the supplying of the dialysate (the substitution) to the dilution channel section A reaches the dialyzer 1. However, the blood concentration of the dilution channel section A may be directly calculated using a certain parameter, such as a theoretical value or the like.

The starting of the control, the control of the flow rate of the dialysate supplied by the substitution pump 9 (the substitution supplying device) using the control device 11 as described above is based on a condition where blood flowing through the dilution channel section A is not diluted by the substitution (the dialysate). For example, as a condition that the blood of the dilution channel section A is not diluted, there are situations, when starting the substitution (that is, when starting to drive the substitution pump 9), when it is determined that the blood concentration measured by the blood densitometer is greater than a predetermined value by disposing the blood densitometer on the dilution channel section A. The fluid pressure of the blood flowing through the dilution channel section A is measured by disposing the pressure gauge on the dilution channel section A. Thus, it is determined that the fluid pressure is greater than a predetermined value. The blood pump 4 is driven by a predetermined amount (for example, the capacity of the dilution channel section A) in a state where the substitution pump 9 is stopped. The blood pump 4 is driven by a predetermined certain flow rate or time in a state where the substitution pump 9 is stopped or the like.

Next, a second embodiment of the present disclosure will be described.

Figure 4:
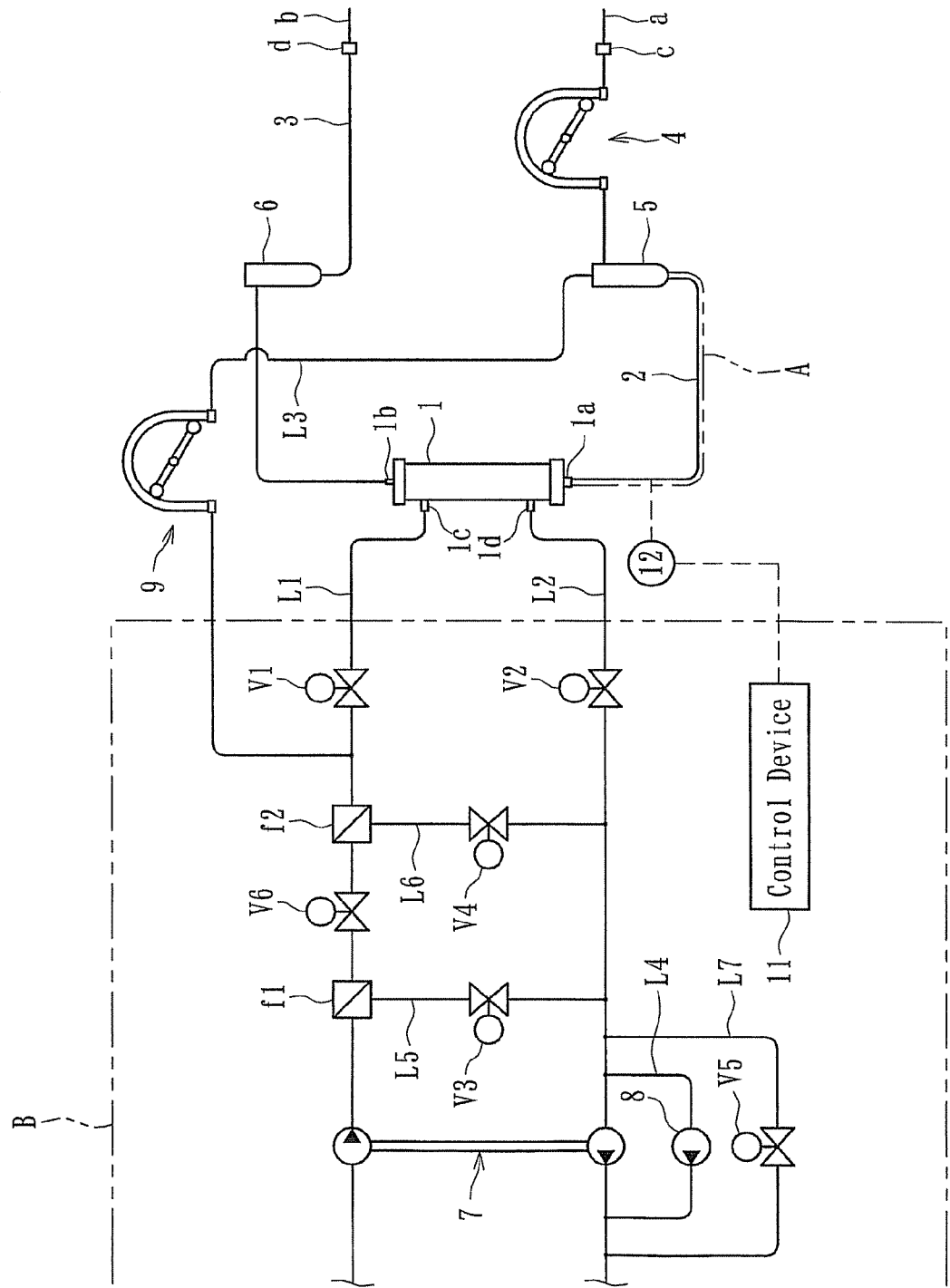
FIG. 4 is a schematic diagram of a dialysis apparatus according to a second embodiment.

As in the first embodiment, a blood purification apparatus in the present embodiment is applied to a blood dialysis apparatus (on-line HDF) that performs a pre-substitution that supplies the dialysate as the substitution to an arterial blood circuit 2 in the blood purification treatment process. As shown in FIG. 4, the blood purification apparatus includes a blood circuit with the arterial blood circuit 2 and a venous blood circuit 3 connected to the dialyzer 1 as the blood purifier. The blood purification apparatus also includes the dialysis apparatus main body B which has the dialysate introduction line L1; a dialysate discharging line L2; the substitution line L3; the substitution pump 9 as a substitution supplying device; the measurement device 12; and the control device 11. The same components as those of the first embodiment are denoted by the same reference numerals. Thus, their detailed descriptions will be omitted.

The measurement device 12 measures the blood concentration of the dilution channel section A. It includes a blood densimeter, for example, a hematocrit sensor or the like that measures a hematocrit value. The blood densimeter is capable of measuring the blood concentration in the dilution channel section A or a sensor that measures the parameter, the pressure of fluid flowing through the dilution channel section A or the like, changes according to the change of the blood concentration. Furthermore, the control device 11 according to the present embodiment is able to control the flow rate of the dialysate (the substitution) supplied by the substitution pump 9 (the substitution supplying device) depending on the blood concentration, including the parameter change according to the blood concentration, measured by the measurement device 12.

According to the present embodiment, the blood concentration of the dilution channel section A can be more accurately grasped compared to a case where the blood concentration of the dilution channel section A is assumed by the calculation device 10. Thus, when performing the pre-substitution, it is possible to more reliably prevent excessive concentration of the blood circulating extracorporeally. Furthermore, the starting of the control, controlling the flow rate of the dialysate supplied by the substitution pump 9 (the substitution supplying device), using the control device 11 is the same as that of the first embodiment.

Figure 5:
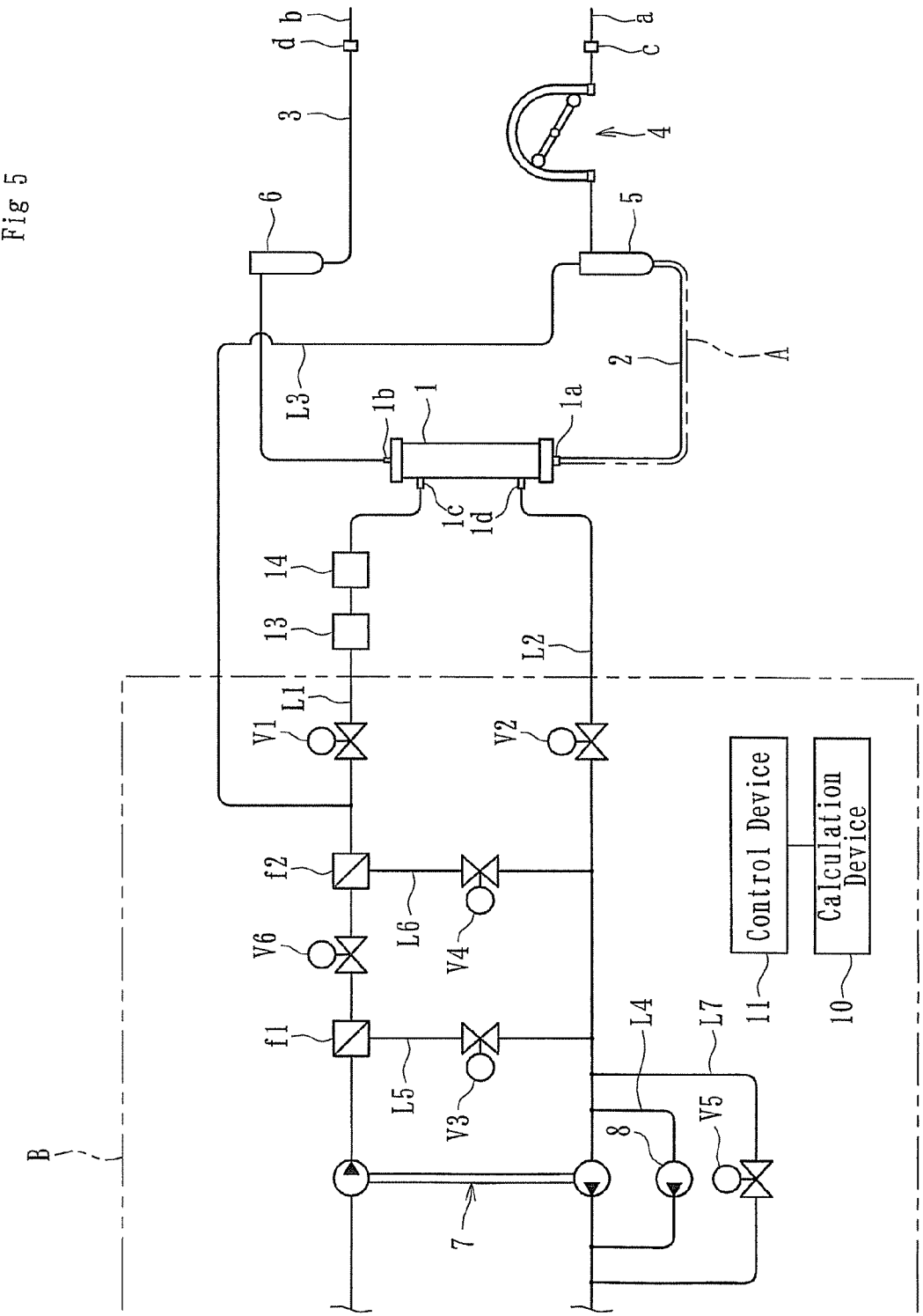
FIG. 5 is a schematic diagram of a dialysis apparatus according to another embodiment.

Although the embodiments have been described as above, the present disclosure is not limited. For example, as shown in FIG. 5, the present disclosure may be applied to a blood dialysis apparatus including a throttle valve 13 (substitution supplying device) that is disposed in the dialysate introduction line 1, instead of the substitution pump 9 disposed in the substitution line L3. The value 13 is able to arbitrarily adjust the flow rate of the dialysate introduced into the dialyzer 1 (the blood purifier). In this case, it is desirable to be able to grasp the flow rate of the dialysate introduced into the delayer 1 and the flow rate flowing through the substitution line L3. A flow meter 14 is disposed near the throttle valve 13 in the dialysate introduction line L1. Furthermore, in FIG. 5, although the calculation device 10 of the first embodiment is included, the measurement device 12 of the second embodiment may be included.

Furthermore, in the present embodiment, while the duplex pump 7 performs the introduction and the discharge of the dialysate, another type (for example, a balancing chamber pump or the like) may be used. Furthermore, although the blood dialysis apparatus according to the present embodiment is illustrated applied to an on-line HDF, for example, the apparatus may be applied to the on-line HF. In this case, for example, in FIGS. 1 and 4, an operation is performed where the filtration from the dialyzer 1 is performed while not causing the dialysate to flow in the dialyzer 1. In this state, the electromagnetic valve V1 is in the opened state and bypassing the dialysate in a state where the electromagnetic valves V4 and V2 are in the opened state. In this manner, although the present embodiment can be applied to the on-line HDF, the on-line HF or the like, the present disclosure can also be applied to a configuration where the substitution is connected to a substitution source such as a substitution bag. The substitution bag accommodates a predetermined amount of the substitution (a form which is not on-line), instead of the configuration where an end of the substitution line is connected to the substitution introduction line L1.

The present device can be provided on a blood purification apparatus including the control device capable of assuming or measuring the blood concentration of the dilution channel section formed of a channel from a connection part to the substitution line to the blood purifier, the arterial blood circuit, and is able to control the flow rate of the substitution supplied by the substitution supplying device based on the assumed or measured blood concentration. Also, the present device can be applied to an apparatus with other added functions.

The present disclosure has been described with reference to the preferred embodiments. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:

1. A blood purification apparatus comprising:
    a blood purifier including a blood purification membrane, the blood purifier performing blood purification in the blood purification membrane;
    an arterial blood circuit having a proximal end connected to the blood purifier;
    a blood pump disposed in the arterial blood circuit;
    a venous blood circuit having a proximal end connected to the blood purifier;
    a dialysate introduction line introducing a dialysate into the blood purifier;
    a dialysate discharge line discharging the dialysate from the blood purifier;
    a substitution line having an end connected to the dialysate introduction line and another end connected to the arterial blood circuit so that the dialysate enters the arterial blood circuit prior to entry into the blood purifier;
    a substitution supplying device capable of supplying substitution flowing in the substitution line to the arterial blood circuit;
    a control device assuming or measuring a blood concentration of a dilution channel section, wherein the dilution channel section is formed by a section of the arterial blood circuit between an arterial air trap chamber and the blood purifier;
    a calculation device for calculating, a time when blood diluted by the supplying of the substitution to the dilution channel section reaches the blood purifier, and assuming the blood concentration of the dilution channel section;
    the control device controlling the flow rate of the substitution supplied by the substitution supplying device depending on the blood concentration assumed by the calculation device in the dilution channel section.

2. The blood purification apparatus according to claim 1, wherein the calculation device calculates a change in concentration of the blood by an operation formula that uses at least one of the following parameters: the flow rate of the blood circulating extracorporeally by the driving of the blood pump; capacity of the dilution channel section; an ultrafiltration flow rate that is an ultrafiltration rate from the blood; an allowance value that can be filtered by the blood purifier; and an objective supply flow rate of the substitution using the substitution supplying device.

3. The blood purification apparatus according to claim 1, further comprising:
    a measurement device for measuring the blood concentration in the dilution channel section;
    the control device is able to control the flow rate of the substitution supplied by the substitution supplying device depending on the blood concentration measured by the measurement device.

4. The blood purification apparatus according to claim 3, wherein the measurement device includes a blood densitometer capable of measuring the blood concentration in the dilution channel section or a sensor that measures parameter changes according to a change of the blood concentration.

5. The blood purification apparatus according to claim 1, wherein the control device is capable of increasing, stepwise, and controlling the flow rate of the substitution supplied by the substitution supplying device.

6. The blood purification apparatus according to claim 1, wherein the control device is capable of continuously increasing and controlling the flow rate of the substitution supplied by the substitution supplying device.

7. A blood purification apparatus comprising:
    a blood purifier including a blood purification membrane, the blood purifier performing blood purification in the blood purification membrane;
    an arterial blood circuit having a proximal end connected to the blood purifier;
    a blood pump disposed in the arterial blood circuit;
    a venous blood circuit having a proximal end connected to the blood purifier;
    a dialysate introduction line introducing a dialysate into the blood purifier;
    a dialysate discharge line discharging the dialysate from the blood purifier;
    a substitution line having an end connected to the dialysate introduction line and another end connected to the arterial blood circuit so that the dialysate enters the arterial blood circuit prior to entry into the blood purifier;

a substitution supplying device capable of supplying substitution flowing in the substitution line to the arterial blood circuit prior to entry into the blood purifier; and a control device assuming or measuring a blood concentration of a dilution channel section, wherein the dilution channel section is formed by a section of the arterial blood circuit between an arterial air trap chamber and the blood purifier by calculating a time when diluted blood, blood and dialysate in the dilution channel section, reaches the blood purifier and the control device controlling the flow rate of the substitution supplied by the substitution supplying device based on the assumed or measured blood concentration in the dilution channel section.

* * * * *

UNITED STATES PATENT AND TRADEMARK OFFICE
CERTIFICATE OF CORRECTION

| | | |
|---|---|---|
| PATENT NO. | : 8,945,037 B2 | Page 1 of 1 |
| APPLICATION NO. | : 13/625315 | |
| DATED | : February 3, 2015 | |
| INVENTOR(S) | : Shinya Hasegawa et al. | |

It is certified that error appears in the above-identified patent and that said Letters Patent is hereby corrected as shown below:

In the Specification

Column 4
Line 17      after "purification", delete ","

Signed and Sealed this
Eleventh Day of August, 2015

Michelle K. Lee
*Director of the United States Patent and Trademark Office*